United States Patent
Lynn et al.

[11] Patent Number: 6,117,682
[45] Date of Patent: *Sep. 12, 2000

[54] METHOD FOR DETECTING HYDROCARBONS IN WATER

[75] Inventors: Theodore B. Lynn, Hamden, Conn.; Keith A. Wright, Camino, Calif.

[73] Assignee: Dexsil Corporation, Hamden, Conn.

[*] Notice: This patent is subject to a terminal disclaimer.

[21] Appl. No.: 09/083,420

[22] Filed: May 22, 1998

Related U.S. Application Data

[63] Continuation-in-part of application No. 08/557,562, Nov. 14, 1995, Pat. No. 5,756,357, which is a continuation-in-part of application No. 08/411,851, Mar. 28, 1995, abandoned, which is a continuation of application No. 08/052,630, Apr. 27, 1993, abandoned.

[51] Int. Cl.$^7$ ............ G01N 33/24; G01N 33/28

[52] U.S. Cl. ............ 436/29; 436/25; 436/27; 436/28; 436/40; 436/60; 436/139; 422/68.1; 73/61.44; 73/863.12

[58] Field of Search ............ 436/25, 28, 29, 436/31, 139, 143, 73, 60; 422/68.1; 73/61.44, 863.12

[56] References Cited

U.S. PATENT DOCUMENTS

| | | | |
|---|---|---|---|
| 2,311,151 | 2/1943 | Campbell | 250/71 |
| 2,312,271 | 2/1943 | Smith | 23/230 |
| 2,431,487 | 11/1947 | Larsen | 250/71 |
| 2,500,213 | 3/1950 | Stevens | 250/43 |
| 2,527,121 | 10/1950 | Dudenbostel, Jr. | 88/14 |
| 2,527,122 | 10/1950 | Heigl et al. | 88/14 |
| 2,712,986 | 7/1955 | Huckabay | 23/230 |
| 3,524,346 | 8/1970 | Schmidt | 73/153 |
| 3,700,409 | 10/1972 | Zall | 23/230 |
| 3,746,511 | 7/1973 | Stookey et al. | 23/231 |
| 3,872,315 | 3/1975 | Boll | 250/575 |
| 4,046,668 | 9/1977 | Farcasiu et al. | 208/11 LE |
| 4,146,799 | 3/1979 | Pitt et al. | 250/574 |
| 4,343,897 | 8/1982 | Neumann et al. | 435/19 |
| 4,485,071 | 11/1984 | Larter | 422/78 |
| 4,595,529 | 6/1986 | Neace | 252/631 |

(List continued on next page.)

OTHER PUBLICATIONS

Zhang et al, Determination of a small amount of crude oil in soil using tetrahydrofuran–turbidimetric method, Huanjing Kexue Journal, Abstract, 9(4), 57–8, 52, 1988.

M.S. Patel, Rapid and Convenient Laboratory Method for Extraction and Subsequent Spectrophotometric Determination of Bitumen Content of Bituminous Sands, Analytical Chemistry, vol. 46, No. 6, pp 794–795, May 1974.

H. Bauer et al, Instrument Analysis, Chap. 7, Ultraviolet and Visible Absorption Spectroscopy, pp. 160–165.

R. Silverstein et al, Spectrometric Identification of Organic Compounds, Third Edition, pp. 248–253.

Test Method No. 418.1 (Spectrophotomeric, Infrared), Petroleum Hydrocarbons, Total Recoverable, pp. 418.1–1–418.1–3, 1978.

Test Method No. 3550A, Ultrasonic Extraction, pp. 3550A–1–3550A–13, Revision 1, Nov. 1992.

*Primary Examiner*—Long V. Le
*Assistant Examiner*—P. Kathryn Bex
*Attorney, Agent, or Firm*—Libert & Associates; Frederick A. Spaeth

[57] ABSTRACT

The presence of hydrocarbons in water is detected by contacting a water sample with an adsorbent material to extract hydrocarbons from the water sample and then contacting the adsorbent material with a solvent for the hydrocarbons. A developer such as a miscible nonsolvent liquid is mixed into the solvent to produce a test mixture. The turbidity of the test mixture is observed to determine the presence of hydrocarbons in the water sample. The nonsolvent may contain at least 0.5% salt, e.g., at least 1%, preferably 5% salt, and an emulsifier. Turbidity may be measured quantitatively by measuring light scattered at 90° to a test light beam or by visual comparison to a reference scale.

17 Claims, 3 Drawing Sheets

COMPARATIVE EXAMPLE

U.S. PATENT DOCUMENTS

| | | | |
|---|---|---|---|
| 4,822,475 | 4/1989 | McDaniel et al. | 208/48 |
| 4,944,921 | 7/1990 | Colby et al. | 422/70 |
| 4,980,295 | 12/1990 | Udy | 436/21 |
| 4,992,379 | 2/1991 | Hanby | 436/29 |
| 5,013,667 | 5/1991 | Lynn et al. | 436/126 |
| 5,028,543 | 7/1991 | Finch et al. | 436/124 |
| 5,104,228 | 4/1992 | Baillie | 356/442 |
| 5,114,567 | 5/1992 | DiFoggio | 208/401 |
| 5,134,359 | 7/1992 | Durley, III et al. | 324/71.1 |
| 5,155,546 | 10/1992 | Balsam et al. | 356/300 |
| 5,181,428 | 1/1993 | Chriswell | 73/863.12 |
| 5,194,921 | 3/1993 | Tambo et al. | 356/432 |
| 5,236,594 | 8/1993 | O'Reilly et al. | 210/656 |
| 5,288,643 | 2/1994 | Sadhir et al. | 436/60 |
| 5,298,967 | 3/1994 | Wells | 356/336 |
| 5,299,453 | 4/1994 | Sprunt et al. | 73/153 |
| 5,306,643 | 4/1994 | Sadhir et al. | 436/140 |
| 5,344,781 | 9/1994 | Kitchen et al. | 436/29 |
| 5,355,736 | 10/1994 | Skogley | 73/863.21 |
| 5,384,262 | 1/1995 | Piasio et al. | 436/518 |
| 5,561,065 | 10/1996 | Schabron | 436/28 |
| 5,576,217 | 11/1996 | Hsu | 436/126 |
| 5,679,574 | 10/1997 | Friedman et al. | 436/29 |

COMPARATIVE EXAMPLE

METHOD FOR DETECTING HYDROCARBONS IN WATER

CROSS-REFERENCE TO RELATED APPLICATIONS

This application is a continuation-in-part of U.S. patent application Ser. No. 08/557,562 in the name of Keith A. Wright et al, filed Nov. 14, 1995, and entitled "METHOD FOR DETECTING HYDROCARBONS IN SOIL", U.S. Pat. No. 5,756,357, which is a continuation-in-part of Ser. No. 08/411,851, Mar. 28, 1995, now abandoned, which is a continuation of Ser. No. 08/052,630, filed Apr. 27, 1993, now abandoned.

BACKGROUND OF THE INVENTION

1. Field of the Invention

This invention relates to a method for detecting hydrocarbons in water and, in particular, to a method comprising extracting the hydrocarbons from the water using an absorbent material and a water-miscible solvent.

It is now well-accepted that corporations and individuals have a legal duty to protect the environment, including water, against contamination by the inadvertent release of oil or other hydrocarbons, and that remedial measures must be taken should such accidents occur. Various tests have been developed to enable investigators to detect the presence of hydrocarbons in water to help identify releases from leaking storage tanks and other sources of contamination.

2. Related Art

U.S. Pat. No. 3,700,409 to Zall, dated Oct. 24, 1972, discloses a method of detecting hydrocarbon contaminants in aqueous solutions. The method involves passing an aqueous sample through fiberglass filter paper and then contacting the filter paper with a small amount of chromic-sulfuric acid. A resultant bluish-green color indicates the presence of hydrocarbons in the aqueous sample.

U.S. Pat. No. 4,146,799 to Pitt et al, dated Mar. 27, 1979, discloses an apparatus for detecting oil in water employing a scatter cell, an infrared laser beam connected to the cell via a fiber optic interface and one or more light scattering detectors (i.e., photocells) all individually connected to the cell via fiber optic interfaces. The scatter cell is dimensioned and configured so that a first photocell is arranged in a direct line with an infrared laser beam and at least one or more photocells are arranged at a relatively small angle (e.g., 20°) to the light source. Compensation circuitry may be employed to nullify small perturbations caused by rust particles.

U.S. Pat. No. 5,355,736 to Skogley, dated Oct. 18, 1994, discloses an apparatus and process for collecting and preparing test samples for analysis of diffused ions therein. The diffused ions are adsorbed by an adsorbent material by contacting the sample with the absorbent material for a substantial amount of time. The ions are then recovered by contacting the adsorbent material with a strong acid or base or a salt solution for later quantitative analysis.

SUMMARY OF THE INVENTION

The present invention provides a method for detecting hydrocarbons in water. According to this method, a water sample is contacted with an adsorbent material capable of adsorbing hydrocarbons. The adsorbent material is contacted with a solvent for the hydrocarbons to extract hydrocarbons therefrom into the solvent. The solvent is mixed with a developer to produce a test mixture that comprises the solvent, the developer and the hydrocarbons extracted from the adsorbent material. The turbidity of the test mixture is observed to determine the presence of hydrocarbons.

According to one aspect of the invention, the developer may comprise a liquid which is miscible with the solvent but which is not a solvent for the hydrocarbons. The nonsolvent liquid developer may be mixed with the solvent in an amount that yields a test mixture comprising from about 30 to 70 weight percent solvent, preferably 30 to 40 weight percent solvent. The solvent preferably comprises at least one alcohol.

According to another aspect of the invention, the method may comprise illuminating the test solution with a test beam from a light source and observing the intensity of light scattered from the source. A test beam having a wavelength in the visable range from about 400 nm to 700 nm may be used to illuminate the test solution. Preferably, a yellow light emitting diode (LED) is used. Further, this may comprise observing scattered light from a point not in the path of the test beam illuminating the test mixture, for example, measuring the intensity of light scattered from the test mixture at an angle of about 90° relative to the test beam.

According to still another aspect of the invention, the method may comprise comparing the turbidity of the test mixture to a reference scale to assess the quantity of hydrocarbons contained in the water sample.

The nonsolvent liquid may also comprise an emulsifier, which may be present in an amount of about 1000 parts per million ("ppm") of the nonsolvent liquid.

Optionally, the adsorbent may comprise cotton.

DETAILED DESCRIPTION OF THE INVENTION AND PREFERRED EMBODIMENTS THEREOF

Figure 1:
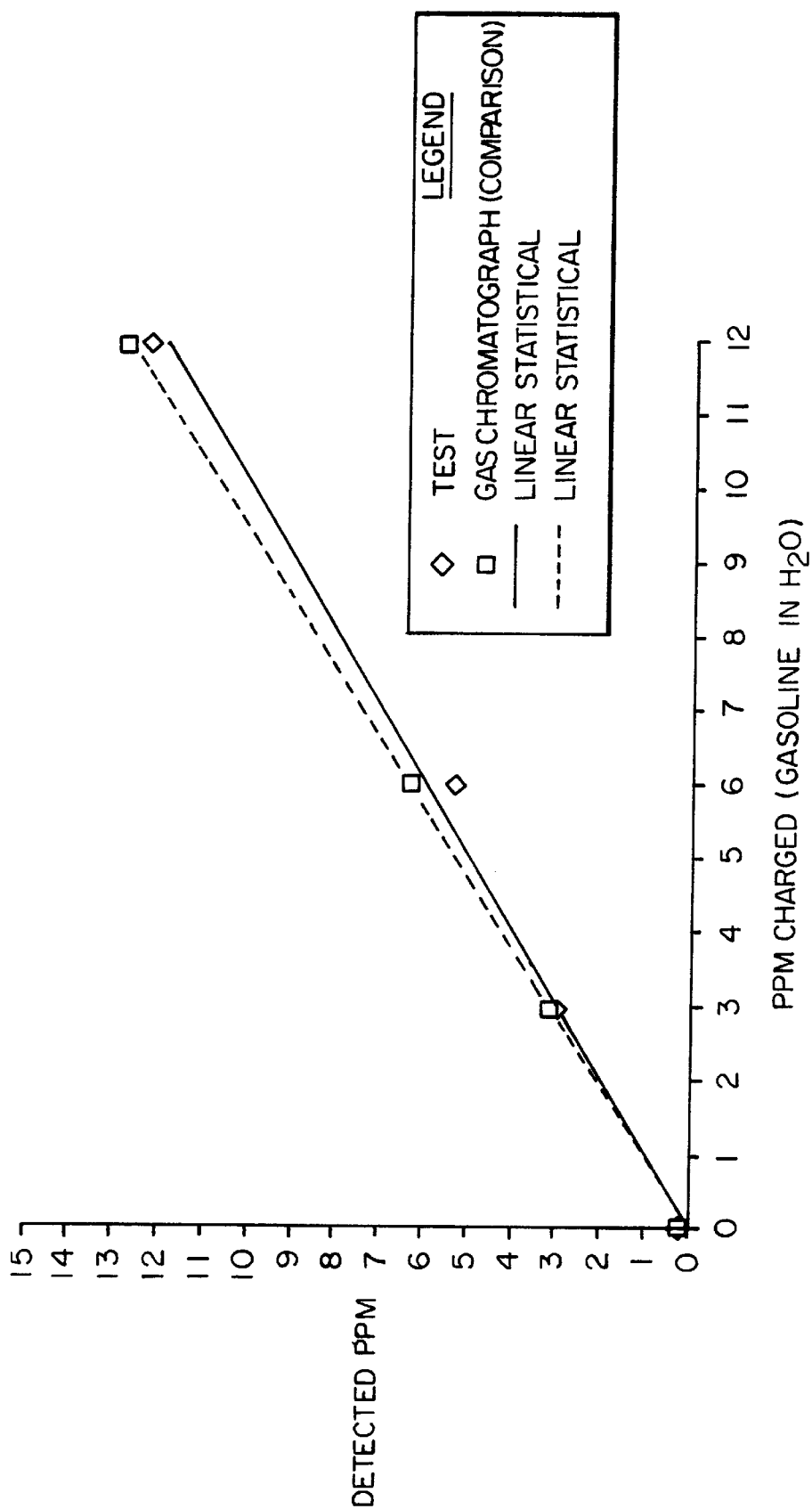
FIG. 1 is a plot comparing the hydrocarbon content of four samples as measured in accordance with the present invention on the vertical axis and as determined by gas chromatography on the horizontal axis.

The present invention relates to a test for the detection of hydrocarbons in water. Broadly described, the method of the present invention involves extracting the hydrocarbons from a water sample by contacting the sample with an adsorbent material capable of adsorbing the hydrocarbons, contacting the adsorbent material with a solvent for hydrocarbons to desorb the adsorbed hydrocarbons therefrom, and then mixing the solvent with a developer to produce a test mixture. The test mixture becomes turbid when hydrocarbons are present therein.

The claimed method provides distinct advantages over prior art methods for the detection of hydrocarbons in water. First, by desorbing the hydrocarbons using a volume of solvent smaller than the volume of the water sample, the concentration of hydrocarbons in the solvent can be "amplified", i.e., the concentration of hydrocarbons in the solvent can be greater than in the water sample, thus making the hydrocarbons easier to detect. Further, by creating a test mixture that becomes turbid in the presence of the hydrocarbons, the claimed method can optionally be practiced without the need for a spectrophotometer or other light-intensity measuring devices or circuitry required in the prior art because the eye is well attuned to the detection of turbidity. The invention thus provides an easily discernible yes/no test for the presence of hydrocarbons. The use of a reference turbidity scale allows a user to make an accurate quantitative assessment of the hydrocarbon content of a sample based on the visually discerned degree of turbidity of the test mixture.

Optionally, the water sample to be tested in accordance with the present invention may be treated to reduce the interfering effect of non-hydrocarbon contaminants that may be present, e.g., soaps and detergents. Such treatment may comprise combining the water sample with a hardening composition that may comprise a strong inorganic acid, such as HCl, a salt such as calcium chloride, and water (preferably deionized water). The hardening composition is combined with the sample before it is contacted with the adsorbent thereby releasing any hydrocarbons from any soaps or detergents that may be present.

Any adsorbent suitable for the adsorption of hydrocarbons may be used in the present invention; such materials are well-known in the art and are commercially available. As discussed below, the adsorbent may be packed in a cylindrical column through which the sample may be flowed. In addition to conventional materials such alumina, silica gel, and C-18 adsorbents, other materials such as cellulose (e.g., in the form of cellulose powder, cotton balls or cotton felt fabric) and/or sintered polypropylene may be used.

Solvents that may be employed in the practice of the present invention include ketones such as methylethylketone, and diethylketone; diethylene glycol, ethylene glycol mono-ethyl-ether; ethylene glycol mono-butylether; polypropylene glycol; triethylene glycol; dimethylsulfoxide; acetonitrile; diethylene glycol dimethyl ether ("diglyme"); tetrahydrofuran (THF); a mixture of about 10–90% acetone with a $C_1$ to $C_6$ alcohol; glacial acetic acid; a mixture of about 10–90% glacial acetic acid with a $C_1$ to $C_6$ alcohol; a mixture of methylethylketone with a $C_1$ to $C_6$ alcohol; and $C_1$ to $C_6$ alcohols and mixtures thereof, methanol being generally preferred. Solvents which are not suitable by themselves for use with the present invention include acetone, ethylacetate ester, petroleum ether, hexane, phenol, methylethylketone, toluene and benzene.

The developer for use in the claimed method may comprise a liquid that is not a solvent for the hydrocarbons. Preferably, however, the developer is miscible with the solvent. Such nonsolvents include distilled water, drinking water, water from a clean freshwater source or other water-based solutions in which hydrocarbons are not soluble. Liquid developers are collectively referred to herein as "nonsolvents". Distilled or deionized water are preferred nonsolvents. Preferably, an aqueous developer is acidified to a pH in the range of 1 to 3 or, more specifically, in the range of 2 to 2.5. A preferred nonsolvent comprises water acidified to a pH of 2.5.

The emulsion formed may become unstable so that, after a short time, the hydrocarbon phase separates from the solvent-nonsolvent phase. To prevent such separation, the Applicants have found that addition of about 1000 parts per million ("ppm") of an emulsifier will be effective to preserve the turbidity of the test mixture.

In a typical embodiment, a nonsolvent liquid developer may comprise water with 1000 ppm of an alkylamine-ethoxylate emulsifying agent available from the Union Carbide Corporation under the trade designation Triton RW-100™ emulsifier pH adjusted to 2.5. This developer may be used in combination with a solvent comprising other emulsifying agents that have been found to be effective include trisodium phosphate, sodium dodecylsulfate, polyoxyethylenesorbitan, and alkylaryl polyether alcohols.

Since the effectiveness of the invention turns on developing turbidity when hydrocarbons are present, the invention is best practiced using clear, i.e., non-opaque, solvents and nonsolvent developers.

The limit of detection, at the 99% confidence level, depends on the volume of water sample used and the hydrocarbon of interest. The method detection limits determination for this method are shown in TABLE I:

TABLE I

| Sample Size | Analyte | Detection Limit |
| --- | --- | --- |
| 1 Liter Sample | Gasoline | 3 ppm |
| 125 ml Sample | Motor Oil | 2 ppm |
| 125 ml Sample | Jet A | 5.5 ppm |
| 125 ml Sample | Diesel Fuel | 6 ppm |

Generally, the invention is practiced as follows. A water sample of known volume is optionally treated with a hardening composition. The solvent is then contacted with the adsorbent material capable of adsorbing hydrocarbons. This may be accomplished by packing a column with the adsorbent and flowing the sample through the column so that the hydrocarbons are adsorbed onto the adsorbent material. The remaining water may be discarded. The adsorbent material is then contacted with a solvent for the hydrocarbons to extract the adsorbed hydrocarbons, if any, that are present therein. For example, an eluent solvent may be flowed through the column having the hydrocarbon-laden adsorbent material therein. The hydrocarbon eluant is thus desorbed from the adsorbent material into the eluent solvent. A developer composition that preferably comprises a nonsolvent liquid is then added to the eluent solvent to create a test mixture. The nonsolvent liquid-to-solvent ratio in the test mixture may be from about 3:1 to 1:3 by volume, i.e., the solvent may comprise from about 25% to 50% of the test mixture, by volume. The turbidity of the test mixture indicates the presence of hydrocarbons therein. Without wishing to be bound by any particular theory, it is believed that turbidity is the result of the formation of an emulsion of the hydrocarbons in the solvent-nonsolvent mixture. Optionally, an aliquot of the hydrocarbon-containing solvent, without a nonsolvent liquid mixed therewith, can be retained or reproduced as a comparative control sample.

The turbidity of the test mixture may be observed in any convenient manner, e.g., by visually observing the test mixture in ambient light. However, in a particular embodiment of the invention, the turbidity of the test mixture is observed by directing a light beam of known intensity into the test mixture and observing the intensity of scattered light emitted therefrom. Many water samples of interest (e.g., waste water, surface water, etc.) are yellow in color. Thus, use of a yellow-colored light-emitting diode (LED) as a light source will reduce absorbance of the light beam. The measured intensity of the scattered light then best represents the amount of scattering resulting from turbidity without significant attenuation from absorption. In a particular embodiment, light of a wavelength of 580 nm may be employed. Preferably, the scattered light is measured from a point where light would not be received from the test beam were the beam to pass through the test mixture. Further, this aspect of the invention provides a measurement technique that differs from most techniques used for spectrographic analysis, in which a test beam is aimed directly at a light-intensity sensor in a path that passes through the solution. A device well-suited to measure the intensity of scattered light is known as a two-channel 90° scattered light meter. As will be shown below, measuring scattered light at an angle of 90° to the test beam as an indication of turbidity yields a more linear indication of hydrocarbon content than measurement of the absorbance of the test mixture at an angle of 180° to the test beam. Such a linear relationship can enable a more accurate estimation of the hydrocarbon content of an unknown test sample.

Since the present invention relies on the development of turbidity in a test mixture to indicate the presence of an analyte (i.e., the substance being determined), it is advantageous to filter the test mixture to remove particulates that would falsely enhance the turbidity of the mixture. A suitable filter system for this purpose is a sintered polyethylene filter having a 20 micron pore size followed by a 0.2 micron pore size filter. The analyte may be filtered using a syringe having filters positioned in the syringe barrel. Disk-type filters may be used, but it is preferred to use filters having greater surface areas than can be attained with a disk-shaped filter. For example, the 20 micron filter may have a conical configuration or may be configured to comprise a plurality of conical protuberances or a hollow cylindrical protuberance, to afford increased surface area.

To obtain a quantitative determination for the presence of hydrocarbons in the water samples, the turbidity of the test mixture can be compared against a reference turbidity scale, e.g., a reference set of turbid mixtures derived from water samples of known hydrocarbon content. This may be achieved by visually comparing the turbidity of the test mixture with the turbidity of a set of laboratory test samples having known hydrocarbon concentrations to determine the concentration of hydrocarbons in the test mixture. Alternatively, a quantitative determination may be made by measuring the intensity of scattered light at an angle 90° to the test beam and comparing the same with a turbidity curve based on like measurements of the intensities of light scattered by a set of samples in a reference set having known concentrations of hydrocarbons.

A "laboratory" reference set can be prepared from a water specimen that is known to be clean, i.e., free of pollutant hydrocarbons. A clean test sample is taken from the specimen and is set aside. A portion of the clean specimen is set aside and the remaining portion is mixed with a known quantity of hydrocarbons such as gasoline or diesel fuel. The specimen and hydrocarbons are mixed together thoroughly so that the specimen portion is uniformly contaminated with the hydrocarbons. Preferably, the hydrocarbon employed is of the same type as that suspected of being present in the water to be tested. A sample is taken from the contaminated portion of the specimen, and an additional, known quantity of the clean portion of the specimen is mixed into the remaining contaminated portion in an amount that reduces the relative pollutant content of the contaminated portion by a convenient amount, e.g., 100 ppm. A sample is taken and another quantity of clean specimen is mixed into the remaining contaminated specimen to further dilute the hydrocarbon content. This procedure is repeated to yield a series of test samples having a steadily decreasing hydrocarbon content. Alternately, the initial test sample may involve a minimal quantity of hydrocarbons and, after the first sample is taken, additional hydrocarbons may be added to the remaining specimen in known amounts, to produce a series of samples of increasing hydrocarbon content. In either case, each set of samples is subjected to a test procedure as described herein. The test mixture derived from the clean test sample will be clear and will represent zero ppm hydrocarbons. The other test mixtures will exhibit varying degrees of turbidity. The turbid mixtures can be retained for as long as the turbidity remains stable and can be used as a reference scale for comparison against tested field samples. Alternatively, a photograph or other visual depiction of each reference sample may be made to provide an illustration reference set for future comparison against a tested field sample. Optionally, the relative turbidities of the reference samples may be measured using a suitable instrument to produce one or both of a turbidity curve or a database against which the turbidity of field samples can be compared.

The method of the claimed invention will be better understood with reference to the following Example:

EXAMPLE 1

A typical test procedure in accordance with one embodiment of the invention is defined below.

Column Preparation

A 10 cubic centimeter ("cc") extraction syringe is fitted with a polypropylene porous frit and is filled with 0.5 grams of a reverse phase C-18 adsorbent material, and is then fitted with a second porous frit, so that the syringe can serve as a reverse phase extraction column. The column is conditioned by flowing 10 milliliters ("ml") of a solvent mixture comprising 60% diglyme, 20% methanol and 20% THF by weight through the column. Then, 50 ml of acidified water is passed over the column and is allowed to stand therein until testing begins.

A 1 liter sample of water in a clean glass container is acidified with 1:1 hydrochloric acid/water to a pH of less than 2. The acidified water was charged with varying concentrations of unleaded gasoline by injection with a standard containing 50,000 ppm gasoline in methyl alcohol. Aliquots of the standard sufficient to yield 0, 3, 6 and 12 ppm of gasoline in the sample were added in sequence, and at each concentration a test sample was taken and tested as described below.

Test

The test sample is loaded into the syringe and is flowed therethrough at 10 ml per minute, and the column is allowed to run dry for 30 seconds. At least some of the hydrocarbons in the water are thus adsorbed onto the column. Then, 10 ml of the diglyme/THF/methyl alcohol solvent described above is pushed through the column at 1 ml per minute as an eluent to desorb the eluant hydrocarbons from the column. The hydrocarbon-contaminated eluate is discharged from the column directly into a 4.5 ml volume of a nonsolvent liquid developer comprising water and 1000 ppm of alkamine-ethoxylate emulsifying agent, acidified to pH=2.5, and the solvent-developer mixture is shaken, producing a turbid test mixture. This test procedure is repeated for each sample resulting in varying degrees of turbidity. The hydrocarbon content of the field sample is determined by comparing the turbidity of the field sample to that of a calibration sample. A hydrocarbon concentration range or, preferably, the approximate hydrocarbon content of the field sample, may be determined by comparing the turbidity of the field sample test mixture to that of the known calibration samples. The calibration sample closest in turbidity to the field sample has a hydrocarbon content that approximates the hydrocarbon content of the field sample.

Four laboratory samples were prepared using deionized water and diesel fuel and each sample was evaluated in two ways. First, the samples were evaluated in accordance with the test described above, except that the turbidity of each turbid test mixture was measured using a yellow LED light source and a light meter positioned at an angle of 90° from the light source. The measured intensities of scattered light were recorded and compared to intensities measured for reference samples. The same samples were then tested using an analytical gas chromatograph, and the results were recorded. The results of the two test methods are plotted in FIG. 1 against the actual hydrocarbon content.

EXAMPLE 2

A series of turbid test mixtures containing varying levels of hydrocarbon content were prepared.

Figure 2:
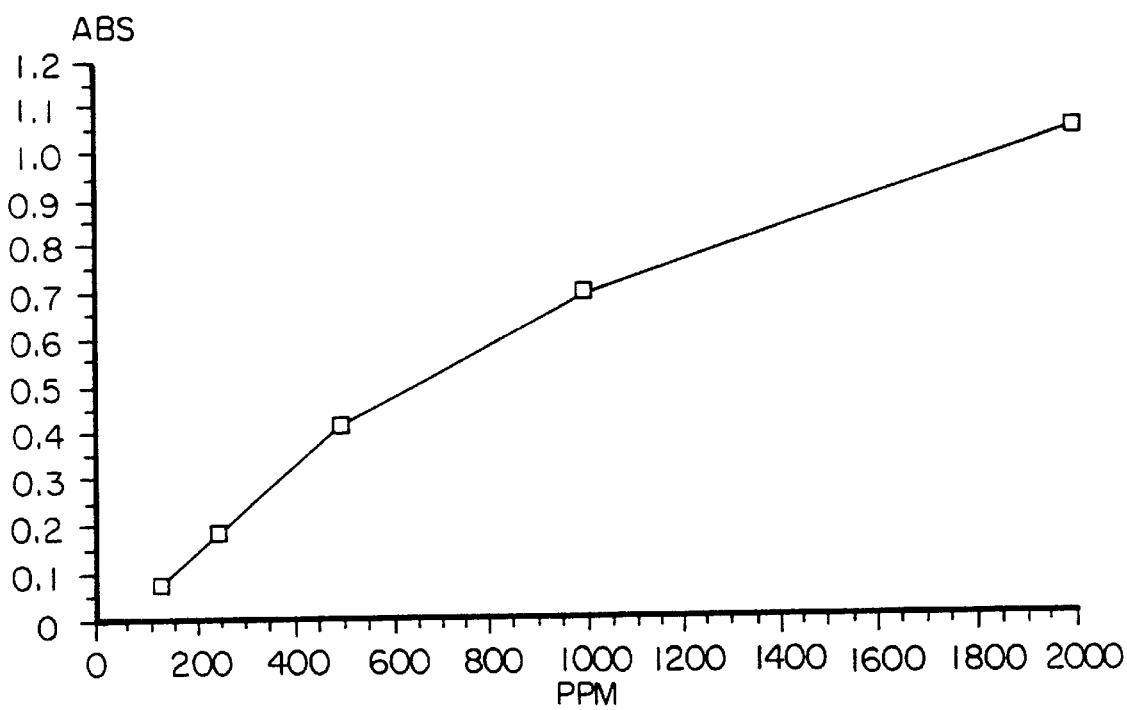
FIG. 2 is a plot of the spectrographic absorbances of five laboratory test mixtures on the vertical axis versus hydrocarbon concentration of the laboratory test mixture on the horizontal axis.

Each test mixture was tested in two ways. First, the absorbance of each test mixture was determined by measuring the light emitted from the mixture at a point 180° in line with the test beam. The results are plotted with absorbance on the vertical axis and hydrocarbon concentration on the horizontal axis, and the results are shown in FIG. 2.

Figure 3:
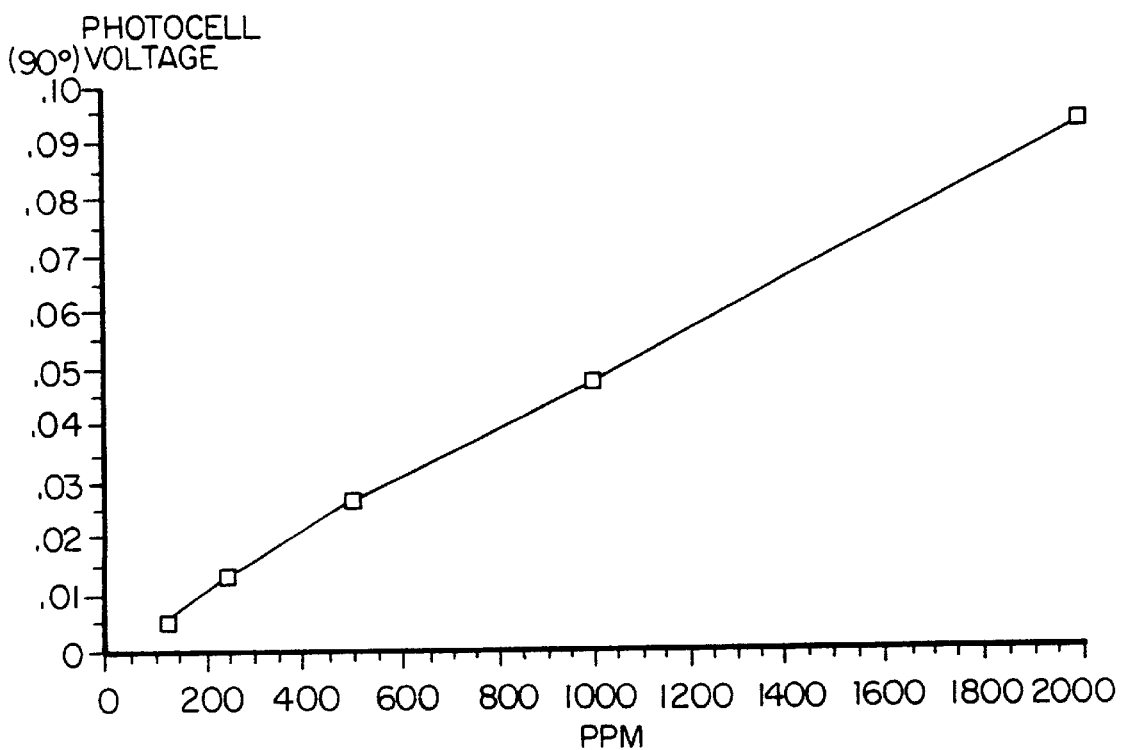
FIG. 3 is a plot of the intensity of light scattered by the test mixtures of FIG. 2 measured in photocell volts on the vertical axis versus hydrocarbon concentration on the horizontal axis, wherein the intensity of the scattered light is measured at 90° relative to the test beam.

Each test mixture was also tested by measuring scattered light emanating from the test tube at an angle of 90° from the test beam. This assured that the reading did not take into account any unscattered portion of the test beam transmitted through the solution that would skew the results of measurements taken at 180°. The results of measurement at 90° are shown in FIG. 3 in which the vertical axis indicates intensity of the measured scattered light and the horizontal axis again indicates hydrocarbon concentration. It is clear by comparing FIGS. 2 and 3 that measurement of scattered light at 90° provides more linear results than that obtained by measuring absorbance at 180°. As a result, fewer reference samples need to be prepared to create an accurate calibration curve using measurements at 90° than are required to accurately plot the curve of measurements at 180°. Thus, this aspect of the invention provides a distinct advantage over the prior art.

EXAMPLE 3

This Example shows that the sensitivity of the method of the present invention varies with the proportion of the solvent to the nonsolvent in the test mixture. For example, TABLE II summarizes varying degrees of turbidity of a variety of test mixtures as measured at an angle of 90° from the light source using an absorbance photometer. To prepare the test mixtures a solvent comprising 20% methyl alcohol (MeOH), 20% THF and 60% diglyme was charged with 500 micrograms per milliliter of both hexadecane and stearic acid. The hydrocarbon-containing solvent was mixed in varying proportions with a liquid developer comprising 1000 ppm RW-100 in water at pH 2.5 and turbidity of the test mixture was measured photometrically. The results are set forth in Table II.

TABLE II

| Volume Developer | Volume Solvent | Test Response |
|---|---|---|
| 3. ml | 3.2 ml | 18 |
| 3.5 ml | 2.7 ml | 121 |
| 4. ml | 2.2 ml | 246 |
| 4.5 ml | 1.7 ml | 144 |
| 5.0 ml | 1.2 ml | 63 |

The data of Table II show that the best response is obtained when the solvent comprises from 27 to 43 percent of the test mixture.

EXAMPLE 4

A water test in accordance with the present invention may be performed as follows.

Twenty ml volumes of sample water charged with known amounts of various hydrocarbons were each deposited in separate malleable polypropylene test tubes. To each tube, a hardening composition comprising 0.5 grams calcium chloride, 0.25 ml concentrated hydrochloric acid and 0.75 ml deionized water is added to the sample. The hardening composition is previously prepared and packaged in a frangible glass ampule. The polypropylene test tube is large enough to hold both the water sample and the ampule so that the user can add the hardening mixture by squeezing the test tube to crush the ampule. The mixture of the sample and the hardening composition may then be mixed by shaking the test tube for a suitable time, e.g., 30 seconds.

The adsorbent material is packed into a syringe-type column containing sintered polypropylene as an adsorbent material. Approximately one-half of the sample is loaded into the column and is forced through the adsorbent using a plunger. The plunger is removed and the remaining portion of the sample is loaded onto the column. The plunger is manually depressed once again to force the second portion of the sample through the adsorbent. It takes approximately 30 seconds for each portion to pass through the adsorbent column. The plunger is removed from the column and then reinserted and advanced once again to dispel any remaining sample water.

To elute the adsorbed hydrocarbons, the plunger is removed from the column and a first solvent comprising a mixture of 1 milliliter methanol and 3 milliliters diglyme are added to the sample tube, shaken and then loaded into the column. The plunger is reinserted into the column and is used to flow the solvent through the column. The eluent solvent is collected from the column in a collection vial. After the first solvent is passed through the adsorbent, a second solvent comprising 1 ml THF is added to the sample tube, shaken and then loaded into the column and is flowed through the adsorbent using the plunger. The second eluent solvent is collected in the same collection vial as the first eluent solvent so that the two are combined.

Figure 4:
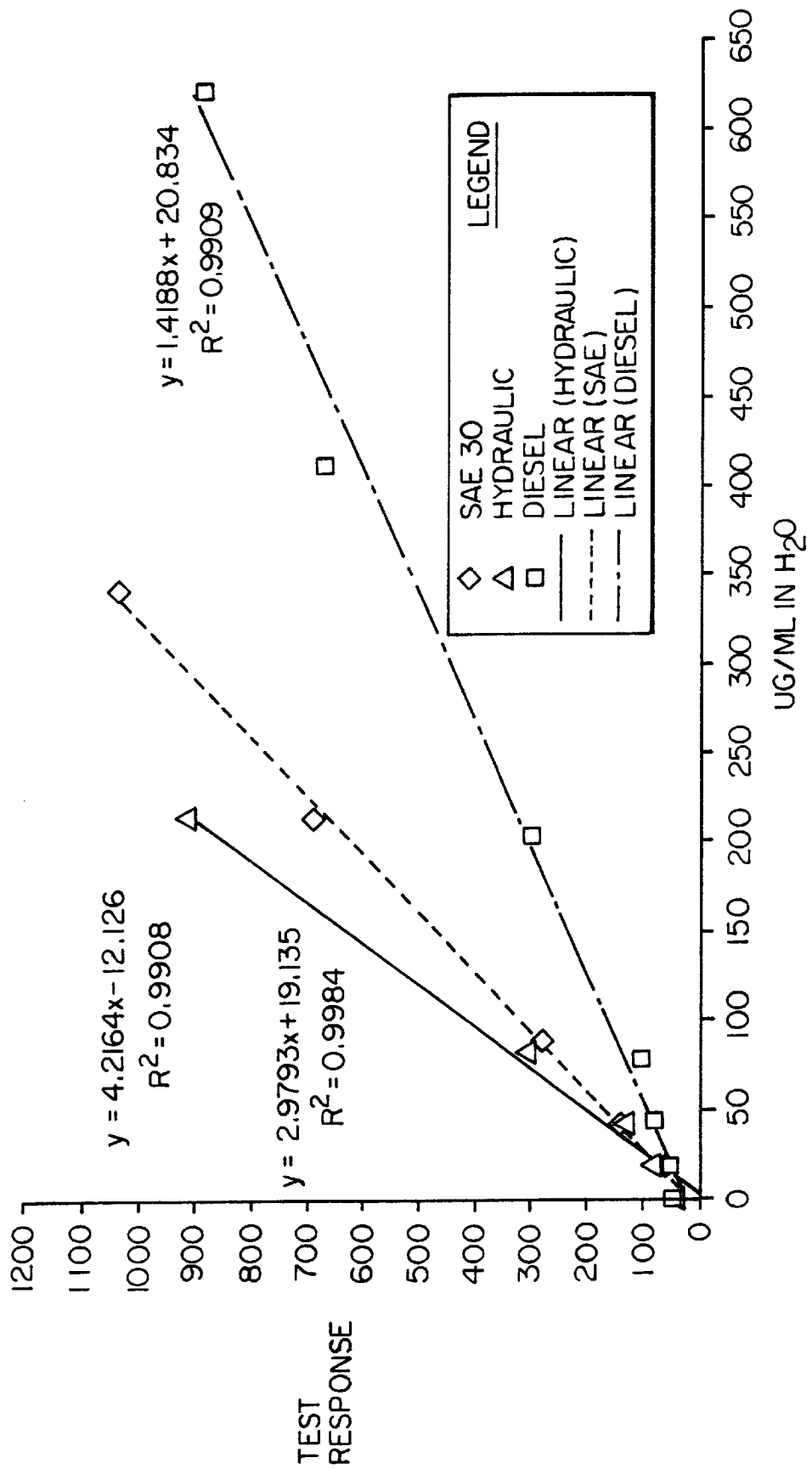
FIG. 4 is a graph showing plots which show actual concentrations of hydrocarbons in several different water samples on the horizontal axis, the results of turbidity measurements of those samples on the vertical axis and formulas relating the measurements to the actual concentrations.

A 2.2 ml aliquot of the combined eluent solvents is combined with 4 ml of an aqueous developer. The developer comprises deionized water acidified to a pH of 2.5 with hydrochloric acid and containing 1000 ppm RW-100™ emulsifier. The resulting test mixture is shaken for 10 minutes and allowed to develop. Turbidity is produced and may be measured as described above. Results are shown in FIG. 4.

While the invention has been described in detail with reference to a particular embodiment thereof, it will be apparent that upon a reading and understanding of the foregoing, numerous variations to the described embodiment will occur to those skilled in the art and it is intended to include such variations within the scope of the appended claims.

What is claimed is:

1. A method for detecting hydrocarbons in water, comprising:
   a) contacting the water with an adsorbent material capable of adsorbing hydrocarbons;
   b) contacting the adsorbent material with a solvent for the hydrocarbons to extract the adsorbed hydrocarbons therefrom;
   c) mixing the solvent with a developer to produce a test mixture comprising the solvent, the developer and the hydrocarbons extracted from the adsorbent material; and
   d) observing the turbidity of the test mixture to determine the presence of hydrocarbons in water.

2. The method of claim 1 wherein the developer comprises a nonsolvent liquid that is miscible with the solvent but which is a nonsolvent for the hydrocarbons.

3. The method of claim 2 comprising mixing the solvent with the nonsolvent liquid in an amount of from about 30% to 50% solvent by weight of the test mixture.

4. The method of claim 3 comprising mixing the solvent with the nonsolvent liquid in an amount of from about 30% to 40% percent solvent by weight, wherein the solvent comprises at least one alcohol.

5. The method of claim 1, claim 2 or claim 3 wherein observing the turbidity of the test mixture comprises illuminating the test solution with a test beam from a light source and observing the intensity of light scattered from the source.

6. The method of claim 5 wherein observing the intensity of light scattered from the source comprises observing scattered light from a point not in the path of the test beam illuminating the test mixture.

7. The method of claim 6 wherein observing the intensity of scattered light comprises measuring the intensity of light scattered from the test mixture at an angle of about 90° relative to the test beam.

8. The method of claim 7 wherein illuminating the test solution comprises producing a test beam having a wavelength from about 400 nm to about 700 nm.

9. The method of claim 7 wherein illuminating the test solution comprises directing light from a yellow light-emitting diode at the test solution.

10. The method of claim 1 or claim 3 further comprising comparing the turbidity of the test solution to a reference scale to assess the quantity of hydrocarbons in the water.

11. The method of claim 2 further comprising mixing the solvent with an aqueous nonsolvent liquid that comprises at least about 0.5% salt.

12. The method of claim 3 or claim 11 comprising mixing the solvent with an aqueous nonsolvent liquid that comprises at least about 1% salt.

13. The method of claim 12 comprising mixing the solvent with an aqueous nonsolvent liquid that comprises about 5% salt.

14. The method of claim 12 wherein the aqueous nonsolvent liquid further comprises an emulsifier.

15. The method of claim 14 wherein the emulsifier comprises about 1000 ppm of the nonsolvent liquid by weight.

16. The method of claim 14 wherein the aqueous developer is adjusted to pH 2.5.

17. The method of claim 1 wherein the adsorbent material comprises cotton.

* * * * *

UNITED STATES PATENT AND TRADEMARK OFFICE
CERTIFICATE OF CORRECTION

PATENT NO. : 6,117,682
DATED : September 12, 2000
INVENTOR(S) : Theodore B. Lynn et al.

It is certified that error appears in the above-identified patent and that said Letters Patent is hereby corrected as shown below:

Column 3,
Line 35, after "such", insert -- as --.

Column 4,
Line 12, replace "effective include" with -- effective, including --.

Column 6,
Line 64, replace "pH=2.5" with -- pH 2.5 --.

Column 7,
Line 65, replace "RW-100" with -- RW-100$^{TM}$ --;

Column 9, claim 4,
Line 29, delete "percent".

Signed and Sealed this

Sixteenth Day of April, 2002

*Attest:*

*Attesting Officer*

JAMES E. ROGAN
*Director of the United States Patent and Trademark Office*